(12) United States Patent
Kridl

(10) Patent No.: US 7,504,563 B1
(45) Date of Patent: *Mar. 17, 2009

(54) METHODS FOR INCREASING STEARATE CONTENT IN SOYBEAN OIL

(75) Inventor: Jean Kridl, Davis, CA (US)

(73) Assignee: Monsanto Technology LLC, St. Louis, MO (US)

( * ) Notice: Subject to any disclaimer, the term of this patent is extended or adjusted under 35 U.S.C. 154(b) by 147 days.

This patent is subject to a terminal disclaimer.

(21) Appl. No.: 11/305,021

(22) Filed: Dec. 19, 2005

Related U.S. Application Data

(63) Continuation of application No. 10/061,280, filed on Feb. 4, 2002, now abandoned, which is a continuation of application No. 09/359,070, filed on Jul. 22, 1999, now Pat. No. 6,380,462, which is a continuation-in-part of application No. 09/134,262, filed on Aug. 14, 1998, now Pat. No. 6,365,802.

(51) Int. Cl.
  *A01H 5/00* (2006.01)
  *C12N 15/82* (2006.01)
(52) U.S. Cl. .................................. 800/312; 800/281
(58) Field of Classification Search ................ None
  See application file for complete search history.

(56) References Cited

U.S. PATENT DOCUMENTS

| | | |
|---|---|---|
| 5,015,580 A | 5/1991 | Christou et al. |
| 5,120,657 A | 6/1992 | McCabe et al. |
| 5,149,655 A | 9/1992 | McCabe et al. |
| 5,416,011 A | 5/1995 | Hinchee et al. |
| 5,420,034 A | 5/1995 | Kridl et al. |
| 5,530,186 A | 6/1996 | Hitz et al. |
| 5,534,425 A | 7/1996 | Fehr et al. |
| 5,557,037 A | 9/1996 | Fehr et al. |
| 5,663,485 A | 9/1997 | Fehr et al. |
| 5,714,668 A | 2/1998 | Fehr et al. |
| 5,750,844 A | 5/1998 | Fehr et al. |
| 5,750,845 A | 5/1998 | Fehr et al. |
| 5,750,846 A | 5/1998 | Fehr et al. |
| 5,760,206 A | 6/1998 | Hitz et al. |
| 5,763,745 A | 6/1998 | Fehr et al. |
| 5,795,969 A | 8/1998 | Fehr et al. |
| 5,945,585 A | 8/1999 | Hitz et al. |
| 5,955,329 A | 9/1999 | Yuan et al. |
| 6,365,802 B2 | 4/2002 | Kridl |

FOREIGN PATENT DOCUMENTS

| | | |
|---|---|---|
| EP | 0301749 B1 | 3/1994 |
| WO | 91/13972 | 9/1991 |
| WO | 91/18985 | 12/1991 |
| WO | 92/11373 | 7/1992 |
| WO | WO 92/20236 | 11/1992 |
| WO | 96/36719 | 11/1996 |
| WO | 97/12047 | 4/1997 |
| WO | 97/26318 | 7/1997 |
| WO | 97/40698 | 11/1997 |

OTHER PUBLICATIONS

Doerks et al, TIG 14(6): 248-250, Jun. 1998.*
Smith et al, Nature Biotechnology 15: 1222-1223, Nov. 15, 1997.*
Brenner, S.E., TIG 15(4): 132-133, Apr. 1999.*
Bork et al, TIG 12(10): 425-427, Oct. 1996.*
DeLuca, V, AgBiotech News and Information 5(6): 225N-229N, 1993.*
Knutzon et al., "Isolation and Characaterization of Two Safflower Oleoyl-Acyl Carrier Protein Thioesterase cDNA Clones", *Plant Physiol.*, 100:1751-1758 (1992).
Beachy et al., "Accumulation and assembly of soybean β-conglycinin in seeds of transformed petunia plants" *EMBO Journal* 4(12):3047-3053 (1985), U.S. Appl. No. 10/061,280.
Berry-Lowe, et al. "The Nucleotide Sequence, Expression, and Evolution of One Member of a Multigene Family Encoding the Small Subunit of Ribulose-1,5-Bisphosphate Carboxylase in Soybean" *Journal of Molecular and Applied Genetics* 1:483-498 (1982), U.S. Appl. No. 10/061,280.
Broun et al., "A bifunctional oleate 12-hydroxylase: desaturase from *Lesquerella fendleri*" *The Plant Journal* 13(2): 201-210 (1998), U.S. Appl. No. 10/061,280.
Chen et al., "Functional analysis of regulatory elements in a plant embryo-specific gene" *Proceedings of the National Academy of Sciences* 83:8560-8564 (1986), U.S. Appl. No. 10/061,280.
Cummins et al., "Differential, temporal and spatial expression of genes involved in storage oil and oleosin accumulation in developing rapeseed embryos: implications for the role of oleosins and the mechanisms of oil-body formation" *Plant Molecular Biology* 23:1015-1027 (1993), U.S. Appl. No. 10/061,280.
Erickson et al., "Property-Enhanced Oils in Food Applications" *Food Technology* 48:63-68 (1994), U.S. Appl. No. 10/061,280.
Gardner et al., "The complete nucleotide sequence of an infectious clone of cauliflower mosaic virus by M13mp7 shotgun sequencing" *Nucleic Acids Research* 9(12):2871-2888 (1981), U.S. Appl. No. 10/061,280.
Graef et al., Biosis Abstract Accession No. 1985:330136, U.S. Appl. No. 10/061,280.

(Continued)

*Primary Examiner*—Elizabeth F McElwain
(74) *Attorney, Agent, or Firm*—Chunping Li; Arnold & Porter, LLP

(57) ABSTRACT

This invention relates to a method for increasing stearate as a component of total triglycerides found in soybean seed. The method generally comprises growing a soybean plant having integrated into its genome a DNA construct comprising, in the 5' to 3' direction of transcription, a promoter functional in a soybean plant seed cell, a DNA sequence encoding an acyl-ACP thioesterase protein having substantial activity on C18:0 acyl-ACP substrates, and a transcription termination region functional in a plant cell. The present invention also provides a soybean seed with about 33 weight percent or greater stearate as a component of total fatty acids found in seed triglycerides.

22 Claims, 4 Drawing Sheets

OTHER PUBLICATIONS

Graef et al., "Inheritance of three stearic acid mutants of soybean" *Crop Science* 25:1076-1079 (1985), U.S. Appl. No. 10/061,280.

Grandbastien et al., "Two soybean ribulose-1,5-bisphosphate carboxylase small subunit genes share extensive homology even in distant flanking sequences" *Plant Molecular Biology* 7:451-465 (1986), U.S. Appl. No. 10/061,280.

Griffiths et al., "The regulation of triacylglycerol biosynthesis in cocoa (*Theobroma cacao*) L." *Planta* 184: 279-284 (1991), U.S. Appl. No. 10/061,280.

Hammond et al., "Registration of A5 Germplasm Line of Soybean (Reg. No. GP44)" *Crop Science* 23:192 (1983), U.S. Appl. No. 10/061,280.

Hartmann et al., "Association of Elevated Stearate with Agronomic and Seed Traits of Soybean" *Crop Science* 37:124-127 (1997), U.S. Appl. No. 10/061,280.

Hawkins et al., "Characterization of acyl-ACP thioesterases of mangosteen (*Garcinia mangostana*) seed and high levels of stearate production in transgenic canola" *The Plant Journal* 13(6):743-752 (1998), U.S. Appl. No. 10/061,280.

International Search Report, PCT/US99/17109 (Jan. 17, 2000), U.S. Appl. No. 10/061,280.

Jefferson et al., "β-Glucuronidase from *Escherichia coli* as a gene-fusion marker" *Proceedings of the National Academy of Sciences* 83:8447-8451 (1986), U.S. Appl. No. 10/061,280.

Jordan et al., "Fatty acid elongation by a particulate fraction from germinating pea" *Biochemical Journal* 191:791-797 (1980), U.S. Appl. No. 10/061,280.

Knutzon et al., "Modification of *Brassica* seed oil by antisense expression of a stearoyl-acyl carrier protein desaturase gene" *Proceedings of the National Academy of Sciences* 89:2624-2628 (1992), U.S. Appl. No. 10/061,280.

Koziel et al., "Optimizing expression of transgenes with an emphasis on post-transcriptional events" *Plant Molecular Biology* 32:393-405 (1996), U.S. Appl. No. 10/061,280.

List et al., "Potential Margarine Oils from Genetically Modified Soybeans" *Journal of the American Oil Chemists' Society* 73(6):729-732 (1996), U.S. Appl. No. 10/061,280.

Liu et al., "An Improved Colorimetric Method for Determining Antitryptic Activity in Soybean Products" *Cereal Chemistry* 66(5):415-422 (1989), U.S. Appl. No. 10/061,280.

Liu et al., "Oxidative Stability of Soybean Oils with Altered Fatty Acid Compositions" *Journal of the American Oil Chemists' Society* 69(6):528-532 (1992), U.S. Appl. No. 10/061,280.

Lundeen et al., "Association of Alleles for High Stearic Acid with Agronomic Characters of Soybean" *Crop Science* 27(6):1102-1105 (1987), U.S. Appl. No. 10/061,280.

McCabe et al., "Stable Transformation of Soybean (*Glycine max*) by Particle Acceleration" *Bio/Technology* 6:923-926 (1988), U.S. Appl. No. 10/061,280.

Mensink et al, "Effect of Dietary Trans Fatty Acids on High-Density and Low-Density Lipoprotein Cholesterol Levels in Healthy Subjects" *New England Journal of Medicine* 323(7):439-445 (1990), U.S. Appl. No. 10/061,280.

Merlo et al., "Ribozymes Targeted to Stearoyl-ACP Δ9 Desaturase mRNA Produce Heritable Increases of Stearic Acid in Transgenic Maize Leaves" *The Plant Cell* 10:1603-1621 (1998), U.S. Appl. No. 10/061,280.

Ohlrogge et al., "Lipid Biosynthesis" *The Plant Cell* 7:957-970 (1995), U.S. Appl. No. 10/061,280.

Ohlrogge et al., "Regulation of Fatty Acid Synthesis" *Annual Review of Plant Physiology and Plant Molecular Biology* 48:109-136 (1997), U.S. Appl. No. 10/061,280.

Rahman et al., "Genetic Control of High Stearic Acid Content in Seed Oil of Two Soybean Mutants", *Theor Appl Genet*, 95:772-776 (1997), U.S. Appl. No. 10/061,280.

Slocombe et al., "Temporal and Tissue-Specific Regulation of a *Brassica napus* Stearoyl-Acyl Carrier Protein Desaturase Gene" *Plant Physiology* 104:1167-1176 (1994), U.S. Appl. No. 10/061,280.

Smith et al., "Antisense RNA inhibition of polygalacturonase gene expression in transgenic tomatoes" *Nature* 334:724-726 (1988), U.S. Appl. No. 10/061,280.

Somerville et al., "Plant Lipids: Metabolism, Mutants, and Membranes" *Science* 252:80-87 (1991), U.S. Appl. No. 10/061,280.

Stam et al., "The Silence of Genes in Transgenic Plants" *Annals of Botany* 79:3-12 (1997), U.S. Appl. No. 10/061,280.

\* cited by examiner

```
CCAAG ATG TTG AAG CTC TCT TCT TCC CGA AGC CCA TTG GCC CGC ATT CCC     50
      Met Leu Lys Leu Ser Ser Ser Arg Ser Pro Leu Ala Arg Ile Pro
                    5                  10                  15

ACC CGG CCC AGG CCC AAC TCC ATT CCT CCC CGG ATA ATT GTG GTT TCC       98
Thr Arg Pro Arg Pro Asn Ser Ile Pro Pro Arg Ile Ile Val Val Ser
             20                  25                  30

TCC TCA TCC AGC AAG GTT AAT CCA AAA CTC AAA ACA GAG GCG GTG GTT TCT  146
Ser Ser Ser Ser Lys Val Asn Pro Lys Leu Lys Thr Glu Ala Val Val Ser
         35                  40                  45

TCG GGG CTG GCT GAC CGG CTC CGG AGC TTG ACC GAG GAC GGG              194
Ser Gly Leu Ala Asp Arg Leu Arg Ser Leu Thr Glu Asp Gly Gly
     50                  55                  60

CTT TCG TAT AAG GAG AAG TTC ATA GTG AGA TGC TAT GAG GTT GGG ATT      242
Leu Ser Tyr Lys Glu Lys Phe Ile Val Arg Cys Tyr Glu Val Gly Ile
         65                  70                  75

AAC AAG ACC GCT ACT GTT GAG ACT ATT GCC AAC CTC TTG CAG GAG GTT      290
Asn Lys Thr Ala Thr Val Glu Thr Ile Ala Asn Leu Leu Gln Glu Val
 80              85                  90                  95
```

FIGURE 1

```
GGA TGC AAT CAC GCC CAA AGC GTT GGA TAT TCG ACG GGT GGG TTT TCG    338
Gly Cys Asn His Ala Gln Ser Val Gly Tyr Ser Thr Gly Gly Phe Ser
            100                 105                 110

ACA ACC CCT ACC ATG AGA AAA TTG CGT CTG ATA TGG GTT ACT GCT CGC    386
Thr Thr Pro Thr Met Arg Lys Leu Arg Leu Ile Trp Val Thr Ala Arg
            115                 120                 125

ATG CAC ATC GAA ATC TAC AAA TAT CCA GCT TGG AGT GAT GTG GTG GAA    434
Met His Ile Glu Ile Tyr Lys Tyr Pro Ala Trp Ser Asp Val Val Glu
            130                 135                 140

ATA GAG TCG TGG GGC CAG GGT GAA GGA AAA ATC GGA ACC AGA CGT GAT    482
Ile Glu Ser Trp Gly Gln Gly Glu Gly Lys Ile Gly Thr Arg Arg Asp
            145                 150                 155

TGG ATT CTG AGA GAC TAT GCC ACT GGT CAA GTT ATT GGC CGA GCT ACT    530
Trp Ile Leu Arg Asp Tyr Ala Thr Gly Gln Val Ile Gly Arg Ala Thr
            160                 165                 170                 175

AGC AAG TGG GTA ATG ATG AAC CAA GAC ACC AGG CGA CTT CAA AAA GTC    578
Ser Lys Trp Val Met Met Asn Gln Asp Thr Arg Arg Leu Gln Lys Val
            180                 185                 190

GAT GTT GAT GTT CGT GAT GAG TAC TTG GTT CAC TGT CCA AGA GAA CTC    626
Asp Val Asp Val Arg Asp Glu Tyr Leu Val His Cys Pro Arg Glu Leu
            195                 200                 205
```

FIGURE 1

AGA TTG GCA TTT CCA GAG GAA AAT AGC AGC TTG AAG AAA ATT TCA     674
Arg Leu Ala Phe Pro Glu Glu Asn Ser Ser Leu Lys Lys Ile Ser
                210                 215                 220

AAA CTT GAA GAT CCT TCT CAA TAT TCG AAG CTG GGG CTT GTG CCT AGA   722
Lys Leu Glu Asp Pro Ser Gln Tyr Ser Lys Leu Gly Leu Val Pro Arg
                225                 230                 235

AGA GCA GAT CTG GAC ATG AAT CAA CAT GTT AAT GTC ACC TAT ATT     770
Arg Ala Asp Leu Asp Met Asn Gln His Val Asn Val Thr Tyr Ile
                240                 245                 250                 255

GGA TGG GTG TTG GAG AGC ATG CCT CAA GAA ATC ATT TAT ACC CAT GAA   818
Gly Trp Val Leu Glu Ser Met Pro Gln Glu Ile Ile Tyr Thr His Glu
                260                 265                 270

CTG CAA ACC ATA ACA TTA GAC TAC AGA TAC AGA TGC CAA CAT GAT GAT   866
Leu Gln Thr Ile Thr Leu Asp Tyr Arg Tyr Arg Cys Gln His Asp Asp
                275                 280                 285

GTG GTT GAT TCC TTG ACT AGT CCA GAG CCT TCT GAA GAT GCT GAA GCA   914
Val Val Asp Ser Leu Thr Ser Pro Glu Pro Ser Glu Asp Ala Glu Ala
                290                 295                 300

GTT TTC AAC CAT AAT GGA ACA AAT GGG TCT GCA AAT GTG AGC GCC AAC   962
Val Phe Asn His Asn Gly Thr Asn Gly Ser Ala Asn Val Ser Ala Asn
                305                 310                 315

FIGURE 1

```
GAC CAT GGA TGC CGC AAC TTT CTG CAT CTA CTA AGA TTG TCG GGC AAT      1010
Asp His Gly Cys Arg Asn Phe Leu His Leu Leu Arg Leu Ser Gly Asn
320                     325                     330                 335

GGA CTT GAA ATC AAC CGT GGT CGT ACT GAG TGG AGA AAG AAA CCT ACA      1058
Gly Leu Glu Ile Asn Arg Gly Arg Thr Glu Trp Arg Lys Lys Pro Thr
            340                     345                     350

AGA TGAGGCAATA AAGTACATTA TGTACTTTAT CGTTGCTTTA GCCGGCTTCT           1111
Arg

GGATGGTGAT TTCTTTCTGC ATTCCTTCTT TCCTTTTTGT TTTCCTAGGG TATCCTTCGC    1171

TTCTTGCCTG TAAGAGTATT ATGTTTTCCG TTTGCCCTGA AGTTGTAAAT TTGTCGAGGA    1231

ACTCGAGTCA TTGTTTGAAT CGAGGATGGT GAGAAGTGTA CTTGTTTGTT GTATTCCATT    1291

CTTCCTGAT                                                            1300
```

FIGURE 1

SEQUENCE LISTING

<160> NUMBER OF SEQ ID NOS: 2

<210> SEQ ID NO 1
<211> LENGTH: 1300
<212> TYPE: DNA
<213> ORGANISM: Garcinia mangostana

<400> SEQUENCE: 1

```
ccaag atg ttg aag ctc tct tct tcc cga agc cca ttg gcc cgc att ccc      50 acc cgg ccc agg ccc aac tcc att cct ccc cgg ata att gtg gtt tcc       98 tcc tca tcc agc aag gtt aat cca ctc aaa aca gag gcg gtg gtt tct      146 tcg ggg ctg gct gac cgg ctc cgg ctg ggc agc ttg acc gag gac ggg      194 ctt tcg tat aag gag aag ttc ata gtg aga tgc tat gag gtt ggg att      242 aac aag acc gct act gtt gag act att gcc aac ctc ttg cag gag gtt      290 gga tgc aat cac gcc caa agc gtt gga tat tcg acg ggt ggg ttt tcg      338 aca acc cct acc atg aga aaa ttg cgt ctg ata tgg gtt act gct cgc      386 atg cac atc gaa atc tac aaa tat cca gct tgg agt gat gtg gtg gaa      434 ata gag tcg tgg ggc cag ggt gaa gga aaa atc gga acc aga cgt gat      482 tgg att ctg aga gac tat gcc act ggt caa gtt att ggc cga gct act      530 agc aag tgg gta atg atg aac caa gac acc agg cga ctt caa aaa gtc      578 gat gtt gat gtt cgt gat gag tac ttg gtt cac tgt cca aga gaa ctc      626 aga ttg gca ttt cca gag gaa aat aat agc agc ttg aag aaa att tca      674 aaa ctt gaa gat cct tct caa tat tcg aag ctg ggg ctt gtg cct aga      722
```

-continued

```
aga gca gat ctg gac atg aat caa cat gtt aat aat gtc acc tat att       770
gga tgg gtg ttg gag agc atg cct caa gaa atc att gat acc cat gaa       818
ctg caa acc ata aca tta gac tac aga cgg gaa tgc caa cat gat gat       866
gtg gtt gat tcc ttg act agt cca gag cct tct gaa gat gct gaa gca       914
gtt ttc aac cat aat gga aca aat ggg tct gca aat gtg agc gcc aac       962
gac cat gga tgc cgc aac ttt ctg cat cta cta aga ttg tcg ggc aat      1010
gga ctt gaa atc aac cgt ggt cgt act gag tgg aga aag aaa cct aca      1058
aga tgaggcaata aagtacatta tgtactttat cgttgcttta gccggcttct           1111
ggatggtgat ttctttctgc attccttctt tccttttgt tttcctaggg tatccttcgc     1171
ttcttgcctg taagagtatt atgttttccg tttgccctga agttgtaaat ttgtcgagga    1231
actcgagtca ttgtttgaat cgaggatggt gagaagtgta cttgtttgtt gtattccatt    1291
cttcctgat                                                            1300
```

<210> SEQ ID NO 2
<211> LENGTH: 352
<212> TYPE: PRT
<213> ORGANISM: Garcinia mangostana

<400> SEQUENCE: 2

```
    Met Leu Lys Leu Ser Ser Arg Ser Pro Leu Ala Arg Ile Pro
                     5                  10                 15
Thr Arg Pro Arg Pro Asn Ser Ile Pro Pro Arg Ile Ile Val Val Ser
                 20                  25                  30
Ser Ser Ser Ser Lys Val Asn Pro Leu Lys Thr Glu Ala Val Val Ser
                 35                  40                  45
Ser Gly Leu Ala Asp Arg Leu Arg Leu Gly Ser Leu Thr Glu Asp Gly
         50                  55                  60
Leu Ser Tyr Lys Glu Lys Phe Ile Val Arg Cys Tyr Glu Val Gly Ile
 65                  70                  75
Asn Lys Thr Ala Thr Val Glu Thr Ile Ala Asn Leu Leu Gln Glu Val
 80                  85                  90                  95
Gly Cys Asn His Ala Gln Ser Val Gly Tyr Ser Thr Gly Gly Phe Ser
                    100                 105                 110
Thr Thr Pro Thr Met Arg Lys Leu Arg Leu Ile Trp Val Thr Ala Arg
                115                 120                 125
Met His Ile Glu Ile Tyr Lys Tyr Pro Ala Trp Ser Asp Val Val Glu
            130                 135                 140
Ile Glu Ser Trp Gly Gln Gly Glu Gly Lys Ile Gly Thr Arg Arg Asp
        145                 150                 155
Trp Ile Leu Arg Asp Tyr Ala Thr Gly Gln Val Ile Gly Arg Ala Thr
160                 165                 170                 175
Ser Lys Trp Val Met Met Asn Gln Asp Thr Arg Arg Leu Gln Lys Val
                180                 185                 190
Asp Val Asp Val Arg Asp Glu Tyr Leu Val His Cys Pro Arg Glu Leu
                195                 200                 205
Arg Leu Ala Phe Pro Glu Glu Asn Asn Ser Ser Leu Lys Lys Ile Ser
            210                 215                 220
Lys Leu Glu Asp Pro Ser Gln Tyr Ser Lys Leu Gly Leu Val Pro Arg
225                 230                 235
Arg Ala Asp Leu Asp Met Asn Gln His Val Asn Asn Val Thr Tyr Ile
```

-continued

```
240                 245                 250                 255
Gly Trp Val Leu Glu Ser Met Pro Gln Glu Ile Ile Asp Thr His Glu
                260                 265                 270

Leu Gln Thr Ile Thr Leu Asp Tyr Arg Arg Glu Cys Gln His Asp Asp
            275                 280                 285

Val Val Asp Ser Leu Thr Ser Pro Glu Pro Ser Glu Asp Ala Glu Ala
        290                 295                 300

Val Phe Asn His Asn Gly Thr Asn Gly Ser Ala Asn Val Ser Ala Asn
    305                 310                 315

Asp His Gly Cys Arg Asn Phe Leu His Leu Leu Arg Leu Ser Gly Asn
320                 325                 330                 335

Gly Leu Glu Ile Asn Arg Gly Arg Thr Glu Trp Arg Lys Lys Pro Thr
                340                 345                 350

Arg
```

METHODS FOR INCREASING STEARATE CONTENT IN SOYBEAN OIL

CROSS-REFERENCE TO RELATED APPLICATIONS

This application is a continuation of U.S. application Ser. No. 10/061,280, filed Feb. 4, 2002 now abandoned, which is a continuation of Ser. No. 09/359,070, filed Jul. 22, 1999, now U.S. Pat. No. 6,380,462, which is a continuation-in-part of U.S. application Ser. No. 09/134,262, filed Aug. 14, 1998, now U.S. Pat. No. 6,365,802. The entirety of these applications are hereby incorporated by reference.

FIELD OF THE INVENTION

The invention relates to genetic modification of plants, plant cells and seeds, particularly altering fatty acid composition.

BACKGROUND

Soybean (*Glycine max*) is one of the highest value crops currently grown in the United States (≈$16 billion in 1996). Ranking close to corn (25%) and wheat (22%), soybean accounted for 19% of the United States crop acres planted in 1994. Often referred to as a "miracle crop", soybean offers tremendous value through the oil, protein and whole soybean products. Agronomic traits, food quality traits related to oils and protein quality are all important for the soybean industry.

More soybeans are grown in the United States than anywhere else in the world (2.4 billion bushels in 1996, 50% of world production). A bushel of soybean (60 pounds) is comprised of 48 pounds of protein meal and 11 pounds of oil. While protein meal is the major component in soybean, oil, lecithin, tocopherols, isoflavones, etc. are all co-products and add value to the bean. Soybean oil is the major edible oil used in the world (40% of the 59.4 million metric tons in 1993). It also accounts for 70% of the 14 billion pounds of edible vegetable oil in the United States. The primary food applications where the oil is used extensively are for baking and frying (40-45%), salad and cooking oil (40-45%), margarine and shortening (15-20%) and a wide spectrum of processed foods. Development of other vegetable oils for specialty uses has recently affected the acreage and production of soybean. The low cost and ready availability of soybean oil provide an excellent opportunity to upgrade this commodity item for specialty uses.

Food fats and oils are chemically composed of triesters of glycerol containing straight chain, normal aliphatic fatty acids, also referred to herein as triacylglycerols or triglycerides (TAG). The properties of food fats and oils are a reflection of the fatty acids contained in the TAG and their distribution on the glycerol backbone. When the melting point of the TAG is below room temperature, the TAG is referred to as an "oil". Triglycerides that melt above room temperature are referred to as "fat". Gradients between fluidity and solidity exist. Partially solidified, non-pourable triglycerides are often referred to as "plastic fats".

Fatty acids are organic acids having a hydrocarbon chain ranging in length from about 4 to 24 carbons. Fatty acids differ from each other in chain length, and in the presence, number and position of double bonds. In cells, fatty acids typically exist in covalently bound forms, the carboxyl portion being referred to as a fatty acyl group. The chain length and degree of saturation of these molecules is often depicted by the formula CX:Y, where "X" indicates number of carbons and "Y" indicates number of double bonds.

Typically, oil derived from commercial soybean varieties is composed of approximately 11% palmitic (C16:0), 4% stearic acid (C18:0), 21% oleic acid (C18:1), 56% linoleic acid (C18:2), and 10% linolenic acid (C18:3). The fatty acid composition of soybean oil, as well as all oils, largely determines its physical and chemical properties, and thus its uses.

Fatty acid biosynthesis has been the subject of research efforts in a number of organisms. For reviews of fatty acid biosynthesis in plants, see Ohlrogge et al., (1995) *Plant Cell*, 7:957-970, Ohlrogge et al., (1997) *Annu Rev Plant Physiol Plant Mol Biol*, 48:109-136 and Sommerville et al. (1991) *Science*, 252:80-87.

As mentioned previously, the fatty acid composition of an oil determines its physical and chemical properties, and thus its uses. Plants, especially plant species which synthesize large amounts of oils in plant seeds, for example soybean, are an important source of oils both for edible and industrial uses. Various combinations of fatty acids in the different positions in the triglyceride will alter the properties of the triglyceride. For example, if the fatty acyl groups are mostly saturated fatty acids, then the triglyceride will be solid at room temperature. In general, however, vegetable oils tend to be mixtures of different triglycerides. The triglyceride oil properties are therefore a result of the combination of triglycerides which make up the oil, which are in turn influenced by their respective fatty acid compositions.

Plant breeders have successfully modified the yield and fatty acid composition of various plant seed oils by introducing desired traits through plant crosses and selection of progeny carrying the desired trait forward. Application of this technique thus is limited to traits which are found within the same plant species. Alternatively, exposure to mutagenic agents can also introduce traits which may produce changes in the composition of a plant seed oil. However, it is important to note that Fatty Acid Synthesis (FAS) occurs in most tissues of the plant including leaf (chloroplasts) and seed tissue (proplastids). Thus, although a mutagenesis approach can sometimes result in a desired modification of the composition of a plant seed oil, it is difficult to effect a change which will not alter FAS in other tissues of the plant.

A wide range of novel vegetable oils compositions and/or improved means to obtain or manipulate fatty acid compositions, from biosynthetic or natural plant sources, are needed. Plant breeding, even with mutagenesis, cannot sufficiently meet this need and provide for the introduction of novel oil.

For example, cocoa-butter has certain desirable qualities (mouthfeel, sharp melting point, etc.) which are a function of its triglyceride composition. Cocoa-butter contains approximately 24.4% palmitate (16:0), 34.5% stearate (18:0), 39.1% oleate (18:1) and 2% linoleate (18:2). Thus, in cocoa butter, palmitate-oleate-stearate (POS) comprises almost 46% of triglyceride composition, with stearate-oleate-stearate (SOS) and palmitate-oleate-palmitate (POP) comprising the major portion of the balance at 33% and 16%, respectively, of the triglyceride composition. Other novel oils compositions of interest might include trierucin (three erucic) or a triglyceride with medium chain fatty acids in each position of the triglyceride molecule.

Plant seed oils contain fatty acids acylated at the sn-1, sn-2, and sn-3 positions of a glycerol backbone, referred to as a triacylglycerol (TAG). The structure of the TAG, as far as positional specificity of fatty acids, is determined by the specificity of enzymes involved in acylating the fatty acyl CoA substrates to the glycerol backbone. For example, there is a tendency for such enzymes from many temperate and tropical crop species to allow either a saturated or an unsaturated fatty acid at the sn-1 or the sn-3 position, but only an unsaturated fatty acid at the sn-2 in the seed TAGs. In some species such as cocoa, TAG compositions suggest that this tendency is carried further in that there is an apparent preference for acylation of the sn-3 position with a saturated fatty acid, if the sn-1 position is esterified to a saturated fatty acid. Thus, there is a higher percentage of structured TAG of the form Sat-Un-Sat (where Sat=saturated fatty acid and Un=unsaturated fatty acid).

Of particular interest are triglyceride molecules in which stearate is esterified at the sn-1 and sn-3 positions of a triglyceride molecule with unsaturates in the sn-2 position particularly oleate. Vegetable oils rich in such SOS (Stearate-Oleate-Stearate) molecules share certain desirable qualities with cocoa butter yet have a degree of additional hardness when blended with other structured lipids. SOS-containing vegetable oils are currently extracted from relatively expensive oilseeds from certain trees grown in tropical areas such as Sal, Shea, and Illipe trees from India, Africa, and Indonesia respectively. Cheaper and more conveniently grown sources for SOS-type vegetable oils are desirable.

In addition, vegetable oils rich in stearate fatty acid content tend to be solid at room temperature. Such vegetable fats can be used directly in shortenings, margarine and other food "spread" products, obviating the need for chemical hydrogenation. Hydrogenation is a process whereby molecular hydrogen is reacted with the unsaturated fatty acid triglyceride until the desired degree of solidity is obtained. The solidity is commonly determined by the solid fat index (SFI, Official and Tentative Methods, American Oil Chemists' Society, Cd 10-57(93), Champaign, Ill.). Values are determined by dilatometry (expansion in volume) over a defined temperature range of 50°, 70°, 80°, 92° and 100° or 104° F. The hydrogenation process converts unsaturated fatty acids to partially or fully saturated fatty acids, and increases the heat and oxidative stability of the product. The iodine value (IV) measures the degree of unsaturation of a fat. Lower values indicate greater saturation. The oxidative stability may be measured by an oil stability index (Official and Tentative Methods, American Oil Chemists' Society, Cd 1b-87, Champaign, Ill.) and active oxygen method (AOM, Official and Tentative Methods, American Oil Chemists' Society, Cd 12h-92, Champaign, Ill.). The cost and any other factors associated with chemical hydrogenation, such as the production of trans fatty acids, can be avoided if the vegetable oil is engineered to be stearate rich in the plant seed.

Moreover, some plant tissues use 18 carbon fatty acids as precursors to make other compounds. These include saturated long chain fatty acids longer than 18 carbons in length. Since very little stearate typically accumulates in soybean plants, it may be necessary to increase stearate accumulation if one wants to increase production of compounds which depend upon supply of stearate fatty acids for synthesis.

The fatty acid composition of soybean oil described above is often considered less than optimal in terms of oil functionality. While the limitations of the fatty acid composition may be partly overcome by chemical hydrogenation, the trans fatty acids produced as a result of the hydrogenation process are Sat-Un-Satpected of having unfavorable health effects (Mensink, et al. (1990) *N. Eng. J. Med.* 323:439-445).

Through the efforts of traditional plant breeding techniques, the fatty acid composition of soybeans has been improved. For example, using mutagenesis, plant breeders have been able to increase the amount of stearate (C18:0) produced in the soybean oil. In such high stearate lines, designated as A6 (ATCC Accession No. 97392, Hammond and Fehr, (1983) *Crop Science* 23:192), stearate levels of up to about 25 weight percent of the total fatty acid composition have been achieved. Such high stearate containing lines have been further bred with mutant soybean lines containing elevated levels of palmitate (16:0). Soybean lines containing the elevated stearate levels produced by mutagenesis demonstrate a negative correlation of increased stearate content and seed yield (Hartmann, et al. (1997) *Crop Science* 37:124-127). Attempts to further increase the stearate content and/or improve the seed yield of such increased stearate lines by breeding have thusfar proven unsuccessful.

List, et al. ((1996) *J. Am. Oil. Chem. Soc.* 73:729-732) describes the use of genetically modified soybean oils in margarine formulations. High stearate oil from soybean variety A6 was found to have an insufficient solid fat index at 24.7° C. and higher temperatures to make margarine. The soybean oil was blended with cottonseed or soybean hardstocks to afford mixtures with sufficient solids content for formulation into margarine.

While soybean based products are a major food source, improvements to the nutritional and commercial quality of this product could add further value to soybean based products. Alteration of the soybean oil content and composition could result in products of higher nutritional content and greater stability. The need for industrial hydrogenation of polyunsaturated oil for food applications could be reduced by the preparation of soybean oil with increased concentrations of stearate.

SUMMARY OF THE INVENTION

The present invention is directed to methods for producing soybean oil having high levels of stearate (C18:0). The method of producing a soybean oil containing increased levels of stearate comprises expression of an acyl-ACP thioesterase capable of producing C18:0 in the seed tissue of the soybean. In particular, the acyl-ACP thioesterase has substantial activity toward 18:0 acyl-ACP substrates, and preferably has little or no activity towards 16:0 acyl-ACP substrates.

The method generally comprises growing a soybean plant containing a construct comprising as operably linked components in the 5' to 3' direction of transcription, a transcription initiation region functional in a seed tissue and a DNA encoding an acyl-ACP thioesterase with substantial activity towards 18:0 acyl-ACP substrates and a transcription termination sequence.

The stearate content of the soybean oil preferably comprises greater than about 20%, more preferably greater than about 33% of the fatty acid moieties in the oil. The oil of the present invention may be used as a blending source to make a blended oil product, or it may also be used in the preparation of food.

In another embodiment of the present invention, a soybean oil having an increased saturated fatty acid composition is provided. Soybean oils with saturated fatty acid compositions of greater than 50 weight percent are exemplified herein.

In yet another embodiment of the instant invention, the novel soybean oil, comprising the increased total saturated fatty acid compositions, provides a novel source of structured TAG of the Sat-Un-Sat (saturated-unsaturated-saturated) form.

The present invention further provides food products and methods for their preparation from a novel soybean [*Glycine max*] seed with increased levels of stearic and oleic acids, and decreased levels of linoleic and linolenic acids under normal growing conditions. The novel soybean seed is produced by a soybean plant obtained from cross pollination of a high stearate plant with a low linolenate plant. There are multiple advantages of a soybean seed with modified fatty acid content. The soybean oil has increased levels of stearic acid, normal levels of palmitic and oleic acids, and decreased levels of linoleic and linolenic acids relative to common soybean oil. Preferably, the soybean oil has a stearic acid composition of above about 15%, a linoleic acid composition below about 45%, and a linolenic acid composition below about 6%. Oil extracted from the soybean seeds possess increased stability and superior cooking characteristics than does oil extracted from standard soybean seeds. The oil has higher levels of solids than does common soybean oil, making it a more preferred material for the preparation of food products such as margarine, tofu, soy flour, soymilk, and shortening. Interesterification of the oil can further enhance the amount of solids present, and the oil's utility in the preparation of food products. Food products prepared from modified soybeans display creamier textures than do food products prepared from common soybeans. While common and high stearate soybean oils require the addition of hardstocks for the formation of margarines and other soy based products, the present oil may be used without the addition of adjuvants.

The novel soybean oil as well as the soybean seed containing the novel oil finds use in many applications.

DESCRIPTION OF THE FIGURES

FIG. 1. Nucleic acid and translated amino acid sequence of a mangosteen FatA-type acyl-ACP thioesterase clone (Garm FatA1) is provided. Garm FatA1 demonstrates primary thioesterase activity on 18:1 acyl-ACP substrate, but also demonstrates substantial activity on 18:0 substrate (approximately 10-20% of 18:1 activity), as well as little or no activity on 16:0 substrates.

DETAILED DESCRIPTION OF THE INVENTION

In accordance with the subject invention, constructs and methods are provided for the production of soybean plants with an increased level of stearate (C18:0), as a percentage of the total fatty acids, in the seed oil. The methods for producing such soybean plants comprise transforming a soybean plant with expression constructs comprising a promoter sequence functional in a plant seed operably linked to a DNA sequence encoding a plant acyl-ACP thioesterase having substantial activity toward 18:0-ACP substrates, preferably those with little or no activity toward 16:0-ACP substrates (hereinafter referred to as stearoyl-ACP thioesterase), and a transcription termination sequence. The expression constructs provide an increase in the levels of stearate fatty acids in the seed oil of the transformed soybean plants.

As described in more detail in the examples that follow, an acyl-ACP thioesterase coding sequence from mangosteen (*Garcinia mangostana*), Garm FatA1 (Hawkins and Kridl (1998) *Plant Journal* 13(6):743-752; and PCT Patent Application WO 96/36719, the entireties of which are incorporated herein by reference) is used in expression constructs to generate transgenic soybean plants with increased production of the stearoyl-ACP thioesterase in host cells. In particular the constructs are used to direct the expression of the Garm FatA1 thioesterase in plant seed cells for modification of triacylglycerol (TAG) fatty acid composition to provide increased levels of C18:0 fatty acyl groups. Furthermore, the constructs of the present invention may find use in plant genetic engineering applications in conjunction with plants containing elevated levels of C18:0 (stearate) fatty acids. Such plants may be obtained by antisense gene regulation of stearoyl-ACP desaturase using methods described by Knutzon et al. (*Proc. Nat. Acad. Sci.* (1992) 89:2624-2628), and may also be obtained by co-suppression using sense expression constructs of the stearoyl-ACP desaturase gene, or by conventional mutation and plant breeding programs. In addition, the constructs and methods for increasing stearate in soybean seed may also find use in plant genetic engineering applications in conjunction with plants containing elevated levels of oleate (C18:1) and/or decreased levels of linoleate (C18:2) fatty acids and/or linolenate (18:3). Such plants with elevated levels of oleate and/or with decreased levels of linoleate and/or linolenate may be obtained through genetic engineering, or by conventional mutation and plant breeding programs.

A plant acyl-ACP thioesterase DNA sequence useful for the preparation of expression constructs for the alteration of stearate levels as described herein encodes for amino acids, in the form of a protein, polypeptide or peptide fragment, which amino acids demonstrate substantial activity on 18:0 acyl-ACP substrates and little or no activity on 16:0-ACP to form 18:0 free fatty acid (i.e., stearate) under plant enzyme reactive conditions. By "enzyme reactive conditions" is meant that any necessary conditions are available in an environment (i.e., such factors as temperature, pH, lack of inhibiting substances) which will permit the enzyme to function.

DNA sequences encoding for acyl-ACP thioesterase enzymes with substantial activity on 18:0 acyl-ACP substrates and little or no activity on 16:0-ACP to form 18:0 free fatty acid (i.e., stearate) are known in the art and are described in Hawkins and Kridl (1998) supra, and PCT Patent Application WO 96/36719. The Garm FatA1 DNA sequence described therein and used herein demonstrates preferential activity on C18:1 acyl-ACP substrate, and also demonstrates substantial activity (approximately 25% of the 18:1 activity) on C18:0 acyl-ACP substrates. Only a small increase in C16:0 activity over activity in control cells is observed, and the 16:0 activity represents only approximately 3% of the 18:1 activity.

In preparing the expression constructs, the various DNA fragments may be manipulated, so as to provide for the DNA sequences in the proper orientation and, as appropriate in the proper reading frame. Towards this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resection, ligation, or the like may be employed, where insertions, deletions or substitutions, e.g. transitions and transversions, may be involved.

For the most part, the constructs will involve regulatory regions functional in plants which provide for modified production of plant stearoyl-ACP thioesterase, and modification of the fatty acid composition. The open reading frame, coding for the plant stearoyl-ACP thioesterase or functional fragment thereof will be joined at its 5' end to a transcription initiation regulatory region such as the wild-type sequence naturally found 5' upstream to the thioesterase structural gene, or to a heterologous regulatory region from a gene naturally expressed in plant tissues. Examples of useful plant regulatory gene regions include those from T-DNA genes, such as nopaline or octopine synthase, plant virus genes, such as CaMV 35S, or from native plant genes.

For such applications when 5' upstream non-coding regions are obtained from other genes regulated during seed maturation, those preferentially expressed in plant embryo tissue, such as ACP, napin and β-conglycinin 7S subunit transcription initiation control regions, as well as the *Lesquerella* hydroxylase promoter (described in Broun, et al. (1998) *Plant Journal* 13(2):201-210 and in U.S. patent application Ser. No. 08/898,038) and the stearoyl-ACP desaturase promoter (Slocombe, et al. (1994) *Plant Physiol.* 104:1167-1176), are desired. Such "seed-specific promoters" may be obtained and used in accordance with the teachings of U.S. Pat. No. 5,420,034 having a title "Seed-Specific Transcriptional Regulation" and in Chen et al., (1986), *Proc. Natl. Acad. Sci.,* 83:8560-8564. Transcription initiation regions which are preferentially expressed in seed tissue, i.e., which are undetectable in other plant parts, are considered desirable for fatty acid modifications in order to minimize any disruptive or adverse effects of the gene product.

Regulatory transcript termination regions may be provided in DNA constructs of this invention as well. Transcript termination regions may be provided by the DNA sequence encoding the plant stearoyl-ACP thioesterase or a convenient transcription termination region derived from a different gene source, for example, the transcript termination region which is naturally associated with the transcript initiation region. The skilled artisan will recognize that any convenient transcript termination region which is capable of terminating transcription in a plant cell may be employed in the constructs of the present invention. As described herein, transcription termination sequences derived from DNA sequences preferentially expressed in plant seed cells are employed in the expression constructs of the present invention.

The method of transformation is not critical to the instant invention; various methods of plant transformation are currently available. As newer methods are available to transform crops, they may be directly applied hereunder. For example, many plant species naturally susceptible to *Agrobacterium* infection may be successfully transformed via tripartite or binary vector methods of *Agrobacterium*-mediated transformation. In addition, techniques of microinjection, DNA particle bombardment, and electroporation have been developed which allow for the transformation of various monocot and dicot plant species.

In developing the DNA construct, the various components of the construct or fragments thereof will normally be inserted into a convenient cloning vector which is capable of replication in a bacterial host, e.g., *E. coli*. Numerous vectors exist that have been described in the literature. After each cloning, the plasmid may be isolated and subjected to further manipulation, such as restriction, insertion of new fragments, ligation, deletion, insertion, resection, etc., so as to tailor the components of the desired sequence. Once the construct has been completed, it may then be transferred to an appropriate vector for further manipulation in accordance with the manner of transformation of the host cell.

Normally, included with the DNA construct will be a structural gene having the necessary regulatory regions for expression in a host and providing for selection of transformant cells. The gene may provide for resistance to a cytotoxic agent, e.g. antibiotic, heavy metal toxin, etc., complementation providing prototrophy to an auxotrophic host, viral immunity or the like. Depending upon the number of different host species in which the expression construct or components thereof are introduced, one or more markers may be employed, where different conditions for selection are used for the different hosts. A number of markers have been developed for use for selection of transformed plant cells, such as those which provide resistance to various antibiotics, herbicides, or the like. The particular marker employed is not essential to this invention, one or another marker being preferred depending on the particular host and the manner of construction.

As mentioned above, the manner in which the DNA construct is introduced into the plant host is not critical to this invention. Any method which provides for efficient transformation may be employed. Various methods for plant cell transformation include the use of Ti- or Ri-plasmids, microinjection, electroporation, DNA particle bombardment, liposome fusion, or the like. In many instances, it will be desirable to have the construct bordered on one or both sides by T-DNA, particularly having the left and right borders, more particularly the right border. This is particularly useful when the construct uses *A. tumefaciens* or *A. rhizogenes* as a mode for transformation, although the T-DNA borders may find use with other modes of transformation.

Various methods of transforming cells of soybean have been previously described. Examples of soybean transformation methods have been described, for example, by Christou et al. U.S. Pat. No. 5,015,580 and by Hinchee et al. U.S. Pat. No. 5,416,011, the entireties of which are incorporated herein by reference.

Once a transgenic plant is obtained which is capable of producing seed having a modified fatty acid composition, traditional plant breeding techniques, including methods of mutagenesis, may be employed to further manipulate the fatty acid composition. Alternatively, additional foreign fatty acid modifying DNA sequence may be introduced via genetic engineering to further manipulate the fatty acid composition.

One may choose to provide for the transcription or transcription and translation of one or more other sequences of interest in concert with the expression of a plant stearoyl-ACP thioesterase in a plant host cell. In particular, the reduced expression of stearoyl-ACP desaturase in combination with expression of a plant stearoyl-ACP thioesterase may be preferred in some applications.

When one wishes to provide a plant transformed for the combined effect of more than one nucleic acid sequence of interest, typically a separate nucleic acid construct will be provided for each. The constructs, as described above contain transcriptional or transcriptional and translational regulatory control regions. The constructs may be introduced into the host cells by the same or different methods, including the introduction of such a trait by the inclusion of two transcription cassettes in a single transformation vector, the simultaneous transformation of two expression constructs, retransformation using plant tissue expressing one construct with an expression construct for the second gene, or by crossing transgenic plants via traditional plant breeding methods, so long as the resulting product is a plant having both characteristics integrated into its genome.

By decreasing the amount of stearoyl-ACP desaturase, an increased percentage of saturated fatty acids is provided. Using anti-sense, transwitch, ribozyme or some other stearoyl-ACP desaturase reducing technology, a decrease in the amount of stearoyl-ACP desaturase available to the plant cell is produced, resulting in a higher percentage of saturates such as one or more of stearate (C18:0), arachidate (C20:0), behenate (C22:0) and lignocerate (C24:0). In rapeseed reduced stearoyl-ACP desaturase results in increased stearate levels and total saturates (Knutzon et al. (1992) *Proc. Nat. Acad. Sci.* 89:2264-2628).

Of special interest is the production of triglycerides having increased levels of stearate. In addition, the production of a variety of ranges of stearate is desired. Thus, plant cells having lower and higher levels of stearate fatty acids are contemplated. For example, fatty acid compositions, including oils, having a 10% level of stearate as well as compositions designed to have up to an approximate 60% level of stearate or other such modified fatty acid(s) composition are contemplated.

As described in more detail in the examples that follow, constructs are prepared to direct the expression of a stearoyl-ACP thioesterase in plant seed tissue. Such expression constructs allow for the increase in 18:0 levels in oils obtained from the seeds of transformed soybean plants.

Increases in the levels of stearate in soybeans transformed to express Garm FatA1 range from 4 fold to approximately 13 fold over the levels obtained in seeds from nontransformed control plants. Additionally, by decreasing the amount of stearoyl-ACP desaturase available to the plant FAS complex in conjunction with an increase of the amount of stearoyl-ACP thioesterase available, a more marked increased percentage of stearate may be obtained. By manipulation of various aspects of the DNA constructs (e.g., choice of promoters, number of copies, etc.) and traditional breeding methods, one skilled in the art may achieve even greater levels of stearate. By expression of a plant stearoyl-ACP thioesterase in seed tissue or a decrease in the expression of stearoyl-ACP desaturase or a combination of both, an increased percentage of stearate can be achieved in soybean. In addition, modified thioesterase encoding DNA sequences may find use for increasing stearate levels in seed tissue. Such modified thioesterase sequences may be obtained as described in PCT Patent Application WO 96/36719.

Surprisingly, in the oil of seeds from T2 soybean lines transformed to express the Garm FatA1 DNA sequence from the β-conglycinin 7S subunit promoter, stearate levels of up to 53 percent as a percentage of the total fatty acid composition are obtained. In addition, in the oil of the initial transformed lines expressing Garm FatA1 DNA sequence from the β-conglycinin 7S subunit promoter increases in the levels of stearate obtained from individual seeds range from about 14 weight percent up to about 53 weight percent. Furthermore, transgenic soybean plants expressing the Garm FatA1 DNA sequence from the napin derived promoter accumulate increased levels of stearate ranging from approximately 20 weight percent up to approximately 45 weight percent in individual seeds of T2 soybean lines. Stearate levels obtained from the oil of individual seeds of nontransformed control soybeans range from approximately 4 weight percent to approximately 6 weight percent. Preferred oil compositions for many applications include 33 weight percent or greater stearate fatty acids as a component of the soybean oil.

In addition, transformed soybean lines containing increased stearate levels of the present invention also demonstrate an increase in the total levels of saturated fatty acids. Transformed soybean lines containing elevated stearate levels also contain increased levels of Arachidic acid (20:0) and Behenic acid (22:0). Increases in 20:0 range from about 3 fold to about 11 fold over the levels of 20:0 obtained from the seed oil of nontransgenic control soybean lines. Increases in 22:0 range from about 2 fold to about 5 fold over the levels of 22:0 obtained from the seed oil of nontransgenic control soybean lines.

Thus, in soybean lines transformed to express a stearoyl-ACP thioesterase in the seed tissue, total saturated fatty acids (16:0, 18:0, 20:0 and 22:0) comprise at least 30 percent of the total fatty acids as a percentage of weight, preferably above 50 weight percent. In some cases, total saturated fatty acid levels of above about 65 weight percent may be obtained.

The novel soybean oil compositions of the present invention comprise increased total saturated fatty acids and provide a novel source of structured TAG of the Sat-Un-Sat form. For oil compositions having greater than about 33 weight percent stearate the Sat-Un-Sat form of TAG may comprise 25 percent or greater of the total TAG composition as a stearate-unsaturated-stearate form of TAG. It is apparent that by utilizing a high oleic acid soybean line that one may produce a soybean oil with a high proportion of a stearate-oleate-stearate form of TAG. An example of such high oleic acid soybean oil is described in PCT Application WO 97/40698.

The present invention further provides food products and methods for their preparation from a novel soybean [*Glycine max*] seed with increased levels of stearic and oleic acids, and decreased levels of linoleic and linolenic acids under normal growing conditions. The novel soybean seed is produced by a soybean plant obtained from cross pollination of a high stearate plant with a low linolenate plant. There are multiple advantages of a soybean seed with modified fatty acid content. The soybean oil has increased levels of stearic acid, normal levels of palmitic and oleic acids, and decreased levels of linoleic and linolenic acids relative to common soybean oil. Preferably, the soybean oil has a stearic acid composition of above about 15%, a linoleic acid composition below about 45%, and a linolenic acid composition below about 6%. Oil extracted from the soybean seeds possess increased stability and superior cooking characteristics than does oil extracted from standard soybean seeds. The oil has higher levels of solids than does common soybean oil, making it a more preferred material for the preparation of food products such as margarine, tofu, soy flour, soymilk, and shortening. Interesterification of the oil can further enhance the amount of solids present, and the oil's utility in the preparation of food products. Food products prepared from modified soybeans display creamier textures than do food products prepared from common soybeans. While common and high stearate soybean oils require the addition of hardstocks for the formation of margarines and other soy based products, the present oil may be used without the addition of adjuvants.

The soybean oil compositions of the present invention containing novel fatty acid compositions may find use in a number of applications, without the need for chemical modifications prior to use as described herein, or as described in PCT application titles "Food Products Containing Structured Triglycerides", PCT/US97/06037, the entirety of which is incorporated herein by reference. The soybean oil of the present invention may find use in the preparation of foods to facilitate cooking or heating applications.

The soybean oils produced by the methods of the present invention may be used in the formation of emulsions comprising water and soybean oil. The soybean oil may be treated by interesterification prior to the formation of an emulsion. As used herein, interesterification refers to the process of rearranging the glyceride structure of fats. Interesterification is accomplished by a chemical reaction in which fatty acids are rearranged on the glycerol molecule without modification of the fatty acids themselves. An emulsion may preferably comprise between about 70% and about 90% by volume soybean oil, and between 10% and about 30% by volume water. The aqueous emulsion may further be defined as margarine. As used herein, the term "margarine" refers to an edible emulsion comprising oil and water that is both solid and spreadable at 25° C.

Alternatively, the soybean seeds containing the modified fatty acid compositions of the present invention, may be used to prepare soymilk. Soymilk may be prepared by the steps of selecting soybean seeds, contacting the seeds with water to form a mixture, heating the mixture, grinding the mixture, and removing the solids to form soymilk. Removal of solids may be accomplished by methods including, but not limited to, filtration, sedimentation and centrifugation. The heating step may comprise heating the mixture to any temperature suitable for the formation of tofu, preferably to a temperature sufficient to inactivate the trypsin inhibitor in the liquid at least about 80% as compared to the trypsin inhibitor activity prior to heating, and most preferably to a temperature between about 90° and about 100° C. Trypsin inhibitor activity may be conveniently assayed using colorimetric method described in Liu and Markakis ((1989), *Cereal Chem* 66(5): 415-422).

Soybean seeds containing the novel soybean oil compositions of the present invention may find use in the preparation of tofu. Tofu may be prepared by the steps of selecting soybean seeds containing soybean oil having oil compositions of the present invention, contacting the seeds with water to form a mixture, heating the mixture, grinding the mixture, removing the solids to form a filtrate, adding a coagulant, and cooling the filtrate to form tofu. The coagulant used may be, but is not limited, to glucono-δ-lactone, lemon juice, sea salt, calcium sulfate or magnesium chloride. Removal of solids may be accomplished by methods including, but not limited to filtration, sedimentation, and centrifugation. The heating step may comprise heating the mixture to any temperature suitable for the formation of tofu, preferably to a temperature sufficient to inactivate the trypsin inhibitor in the liquid at least about 80% as compared to the trypsin inhibitor activity prior to heating, and most preferably to a temperature between about 90° and about 100° C. Trypsin inhibitor activity may be conveniently assayed using colorimetric method described in Liu and Markakis ((1989), *Cereal Chem* 66(5): 415-422). The cooling step may comprise cooling the filtrate to any temperature suitable for the formation of tofu, and more preferably to between about 0° C. and about 25° C.

Soy flour may also be prepared from soybean seeds containing the oil compositions of the present invention. A method for preparation of soy flour comprises the steps of selecting soybean seeds and grinding the seeds to produce soy flour. Preferably, the soybean seeds contain soybean oil having increased levels of stearate. The grinding step may be performed by any means suitable for the production of soy flour, including, but not limited to, grinding with wheels, mortar and pestle, plates and blades.

The soybean oil of the present invention may be further used to prepare shortenings. As used herein, the term "shortening" refers to fats, usually plastic in nature, that provide functional effects related to structure, texture and the eating qualities of a variety of food products. The shortening prepared based on the soybean oil of the present invention may also include the incorporation of emulsifiers or surfactants (selected from 21 C.F.R. 172), such emulsifiers used to provide additional functional effects in the final food product. The shortening based on the soybean oil of the present invention may also include a variety of hardstocks (fully hydrogenated triglycerides sourced from a variety of common food oils) that could be used to modify or augment the SFC of the final product and, hence, the physical properties and functionality of the final blend. The plasticity and crystal structure of the final shortening composition based on the soybean oil of the present invention, whether emulsified or not, may be further modified through the process of controlled crystallization and specific gravity reduction known as votation. In this process, the molten shortening described variously above is fed through a scraped-surface heat exchanger, and crystallized in a directed manner-usually in the most functional crystalline form. During this process, a gas is usually whipped into the solidifying product to adjust the specific gravity of the shortening product, and hence its plasticity. This is done, primarily, to enhance the handling characteristics of the final shortening and to allow it to be better incorporated into a variety of food product systems. The emulsifier may generally be any material suitable for the preparation of shortening, preferably an emulsifier approved as a food additive per 21 C.F.R. § 172, and more preferably is a monoglyceride. The use of the novel soybean oil of the present invention may allow for a reduced level of emulsifier addition to achieve the same functional effects as would be required in a standard soybean oil based shortening arrived at through hydrogenation to attain equal solids.

The soybean seeds, oil, and products therefrom may also find use in a number of additional applications known to the art, including the use in various animal feed applications.

The invention now being generally described, it will be more readily understood by reference to the following examples which are included for purposes of illustration only and are not intended to limit the present invention.

EXAMPLES

Example 1

Plant Expression Vector Construction

Plant vectors are constructed to control the expression of a member of the FatA class of acyl-ACP thioesterases from *Garcinia mangostana* (Garm FatA1, Hawkins and Kridl (1998) supra, and PCT Patent Application WO 96/36719) in seeds of soybean utilizing different seed enhanced promoters.

A plant transformation construct, pWRG5374, is prepared to express Garm FatA1 in the embryo tissue of the soybean seed utilizing the napin promoter. A DNA fragment containing the napin 5'/Garm FatA1/napin 3', described in Hawkins and Kridl (1998) supra, is cloned into a vector containing the selectable marker β-glucuronidase (GUS, Jefferson et al., *Proc. Natl. Acad. Sci.* (1986) 83:8447-8451) driven by the CAMV 35S (Gardner, et al. (1981) *Nucleic Acids Res.* 9:2871-2888) promoter. The GUS gene contains an untranslated leader sequence derived from a soybean ribulose-bisphosphate carboxylase (RuBisCo) small subunit, (Grandbastien, et al. (1986) *Plant Mol. Biol.* 7:451-466), ssuL and a translational termination sequence derived from the soybean RuBisCo, (Berry-Lowe (1982) *Jour. Mol. Appl. Genet.* 1:483-498), SpA. Examples of vectors utilizing a GUS selectable marker are described in European Patent 0 301 749 B1, the entirety of which is incorporated herein by reference. The resulting expression construct, pWRG5374, contains the napin 5'/Garm FatA1/napin 3' sequences as well as the 35S-ssuL/GUS/SpA 3' for transgenic selection by indigo blue staining.

The soybean transformation construct, pWRG5378, containing the Garm FatA1 coding sequence expressed from the β-conglycinin 7S subunit promoter was prepared as follows. The Garm FatA1 coding sequence and napin 3' poly-A termination sequences were obtained from plasmid pCGN5253 (described in Hawkins and Kridl (1998) supra). A soybean expression plasmid pWRG5375 was constructed by insertion of the Garm FatA 1 coding and napin 3' sequences downstream of a heterologous promoter from the soybean α' subunit of β-conglycinin (soy 7s, (Chen et al., (1986), *Proc. Natl. Acad. Sci.*, 83:8560-8564)). A 941 bp BamHI-XhoI fragment containing the soy 7s promoter was ligated with a 5186 bp fragment from plasmid pCGN5253 produced by partial digestion with KpnI and complete digestion with SalI. Additionally, an 8 bp BamHI-KpnI adapter having the DNA sequence 5'-GATCGTAC-3' was used to fuse the BamHI site from the soy 7s promoter fragment with the KpnI site from pCGN5253. The resulting plasmid was named pWRG5375. A 3477 bp SacII fragment from plasmid pWRG5375 containing the soy 7s/Garm FatA1/napin 3' was ligated to a 6135 bp fragment containing the α-glucuronidase (GUS) marker cassette (described above) for selection of transgenic soybean plants. The soy 7s/Garm FatA1/napin 3' cassette was inserted such that the transcription of the GUS gene was in the same direction as that of the Garm FatA1 coding sequence. The resulting 8329 bp plasmid was designated as pWRG5378.

Example 2

Soybean Transformation with Garm FatA1 Constructs

Plasmids pWRG5374 and pWRG5378 were digested with NotI and linearized fragments containing both the chimeric Garm FatA1 coding sequence and GUS expression cassettes were purified by HPLC. The linear DNA fragments were stably introduced into soybean (Asgrow variety A5403) by the method of McCabe, et. al. (1988) *Bio/Technology* 6:923-926.

Transformed soybean plants are identified by indigo blue staining of seed tissue with 1 mM X-Gluc (Clontech), 0.1 M NaPO$_4$ (pH 7.0), 0.5 mM potassium ferrocyanide.

Example 3

Fatty Acid Compositional Analysis

Fatty acid compositions were analyzed from seed of soybean lines transformed with pWRG5374 or pWRG5378. One to five seeds of each of the transgenic and control soybean lines were ground individually using a tissue homogenizer (Pro Scientific) for oil extraction. Oil from ground soybean seed was extracted overnight in 1.5 ml heptane containing triheptadecanoin (0.50 mg/ml). Aliquots of 200 μl of the extracted oil was derivatized to methyl esters with the addition of 500 μl sodium methoxide in absolute methanol. The derivatization reaction was allowed to progress for 20 minutes at 50° C. The reaction was stopped by the simultaneous addition of 500 μl 10% (w/v) sodium chloride and 400 μl heptane. The resulting fatty acid methyl esters extracted in hexane were resolved by gas chromatography (GC) on a Hewlett Packard model 6890 GC. The GC was fitted with a Supelcowax 250 column (30 m, 0.25 mm id, 0.25 micron film thickness)(Supelco, Bellefonte, Pa.). Column temperature was 175° C. at injection and the temperature programmed from 175° C. to 245° C. to 175° C. at 40° C./min. Injector and detector temperatures were 250° C. and 270° C., respectively.

The results of the fatty acid compositional analysis from seed oil of the initial transformed 5374 soybean lines is provided in Table 1. Averages are provided where oil compositional analysis was performed on more than one seed from the initial transformant. In seed of transgenic soybean plants expressing Garm FatA1 from the napin promoter, stearate (C18:0) levels were significantly increased over the levels obtained from the seed oil of nontransformed control plants. The increase in stearate is primarily at the expense of oleate, and to a lesser degree linoleate and palmitic all of which were decreased in the transgenic lines. In addition, increases in all saturates examined greater than C18:0 were observed.

TABLE 1

| STRAIN ID | GUS | % 16:0 | % 18:0 | % 18:1 | % 18:2 | % 18:3 | % 20:0 | % 22:0 |
|---|---|---|---|---|---|---|---|---|
| 5374-A5403-3 | + | 6.71 | 24.88 | 14.53 | 43.73 | 6.99 | 1.84 | 1.03 |
| 5374-A5403-3 | + | 6.62 | 26.52 | 11.9 | 44.89 | 7.15 | 1.8 | 0.9 |
| 5374-A5403-3 | + | 7.59 | 22.99 | 13.17 | 45.32 | 8.19 | 1.63 | 0.84 |
| 5374-A5403-3 | + | 7.28 | 23.1 | 13 | 43.65 | 9.74 | 1.88 | 1.13 |
| 5374-A5403-3 | + | 7.39 | 26.54 | 8.4 | 41.95 | 12.38 | 1.9 | 1.07 |
| AVERAGE | | 7.12 | 24.81 | 12.2 | 43.91 | 8.89 | 1.81 | 0.99 |
| 5374-A5403-4 | + | 7.38 | 20.81 | 16.45 | 46.61 | 5.99 | 1.57 | 0.87 |
| 5374-A5403-4 | + | 7.96 | 18.28 | 14.69 | 47.93 | 8.29 | 1.54 | 0.96 |
| 5374-A5403-4 | + | 10.02 | 9.64 | 22.78 | 49.41 | 6.02 | 0.91 | 0.79 |
| 5374-A5403-4 | + | 9.24 | 12.54 | 23.06 | 45.97 | 5.9 | 1.17 | 0.8 |
| 5374-A5403-4 | + | 7.41 | 20.07 | 13.42 | 45.91 | 10.32 | 1.55 | 0.97 |
| AVERAGE | | 8.40 | 16.27 | 18.08 | 47.17 | 7.29 | 1.35 | 0.88 |
| 5374-A5403-14 | + | 7.96 | 38.39 | 7.82 | 37.34 | 6.23 | 2.41 | 1.07 |
| 5374-A5403-35 | + | 9.24 | 33.53 | 11.14 | 38.15 | 7.54 | 1.97 | 0.9 |
| 5374-A5403-36 | + | 8.18 | 19.37 | 13.92 | 47.05 | 8.47 | 1.6 | 1.06 |
| 5374-A5403-36 | + | 7.5 | 19.99 | 13.49 | 47.15 | 8.99 | 1.59 | 0.95 |
| 5374-A5403-36 | + | 7.05 | 23.44 | 10.54 | 46.19 | 9.64 | 1.82 | 0.99 |
| 5374-A5403-36 | + | 7.83 | 20.06 | 13.53 | 47.27 | 8.45 | 1.57 | 0.94 |
| 5374-A5403-36 | + | 7.49 | 22.9 | 11.81 | 46.14 | 8.54 | 1.72 | 1.03 |
| AVERAGE | | 7.61 | 21.15 | 12.66 | 46.76 | 8.82 | 1.66 | 0.99 |
| 5374-A5403-172 | + | 7.92 | 15.53 | 29.9 | 38.2 | 5.8 | 1.36 | 0.89 |
| 5374-A5403-172 | + | 7.37 | 22.45 | 16.63 | 44.3 | 6.58 | 1.56 | 0.77 |
| 5374-A5403-172 | + | 8.74 | 14.38 | 20.17 | 47.33 | 6.94 | 1.17 | 0.84 |
| AVERAGE | | 8.01 | 17.45 | 22.23 | 43.28 | 6.44 | 1.36 | 0.83 |
| Control | | | | | | | | |
| A5403 | − | 11.62 | 4.3 | 24.26 | 49.84 | 7.47 | 0.48 | 0.57 |
| A5403 | − | 12.32 | 4.24 | 21.93 | 52.32 | 7.49 | 0.44 | 0.46 |
| A5403 | − | 12.64 | 4.25 | 20.49 | 53.42 | 7.81 | 0.43 | 0.51 |
| A5403 | − | 12.17 | 4.22 | 21.56 | 52.48 | 8.15 | 0.44 | 0.51 |
| A5403 | − | 11.68 | 4.32 | 25.68 | 49.67 | 7.06 | 0.48 | 0.54 |
| AVERAGE | | 12.09 | 4.27 | 22.78 | 51.55 | 7.60 | 0.45 | 0.52 |

Selected T2 lines also show the trends of increased stearate, and decreased palmitate, oleate and linoleate levels in the seed oil (Table 2). Furthermore, in seed of T2 5374 soybean lines (T3 seed), stearate levels as high as approximately 45% of the fatty acid methyl esters are observed. These levels are increased from approximately 34% in the T1 generation. While null progeny which do not contain the Garm FatA1 transgene contain approximately 4.5% of the fatty acid methyl esters as stearate.

TABLE 2

| STRAIN ID | GUS | 16:0 | 18:0 | 18:1 | 18:2 | 18:3 | 20:0 | 22:0 |
|---|---|---|---|---|---|---|---|---|
| 5374-A5403-3-417 | + | 6.57 | 37.18 | 7.39 | 35.38 | 9.36 | 2.68 | 1.2 |
| 5374-A5403-3-417 | + | 6.52 | 38.66 | 8.26 | 33.82 | 8.43 | 2.78 | 1.29 |
| 5374-A5403-3-417 | + | 6.23 | 39.26 | 7.26 | 35.11 | 7.84 | 2.8 | 1.26 |
| 5374-A5403-3-417 | + | 6.75 | 33.55 | 8.91 | 37.69 | 9.13 | 2.51 | 1.19 |
| 5374-A5403-3-417 | + | 6.18 | 42.21 | 5.88 | 33.36 | 7.99 | 2.94 | 1.23 |
| average | | 6.45 | 38.17 | 7.54 | 35.07 | 8.55 | 2.74 | 1.23 |
| 5374-A5403-35-483 | + | 5.78 | 45.64 | 6.3 | 31.86 | 6.15 | 2.95 | 1.16 |
| 5374-A5403-35-483 | + | 5.82 | 38.21 | 7.83 | 37.06 | 7.22 | 2.54 | 1.12 |
| 5374-A5403-35-483 | + | 5.84 | 38.37 | 7.44 | 37.91 | 6.43 | 2.59 | 1.22 |
| 5374-A5403-35-483 | + | 5.74 | 41.56 | 6.31 | 35.4 | 6.98 | 2.71 | 1.12 |
| 5374-A5403-35-483 | + | 5.58 | 40.35 | 7.06 | 36.91 | 6.11 | 2.63 | 1.16 |

TABLE 2-continued

| STRAIN ID | GUS | 16:0 | 18:0 | 18:1 | 18:2 | 18:3 | 20:0 | 22:0 |
|---|---|---|---|---|---|---|---|---|
| average | | 5.75 | 40.83 | 6.99 | 35.83 | 6.58 | 2.68 | 1.16 |
| 5374-A5403-172-401 | + | 6.73 | 23.12 | 15.02 | 46.04 | 6.05 | 1.77 | 0.97 |
| 5374-A5403-172-401 | + | 6.92 | 21.96 | 14.85 | 46.47 | 6.7 | 1.78 | 1.02 |
| 5374-A5403-172-401 | + | 6.49 | 24.15 | 14.11 | 45.74 | 6.46 | 1.83 | 0.96 |
| 5374-A5403-172-401 | + | 6.83 | 23.09 | 13.64 | 46.56 | 6.85 | 1.79 | 0.96 |
| 5374-A5403-172-401 | + | 8.32 | 20.32 | 11.94 | 47.05 | 9.36 | 1.69 | 1.02 |
| average | | 7.06 | 22.53 | 13.91 | 46.37 | 7.08 | 1.77 | 0.99 |
| 5374-A5403-36-353 | + | 6.18 | 30.73 | 11.36 | 41.3 | 7.3 | 1.92 | 0.89 |
| 5374-A5403-36-353 | + | 6.42 | 30.82 | 11.14 | 41.03 | 7.53 | 1.85 | 0.85 |
| 5374-A5403-36-353 | + | 6.43 | 30.03 | 11.61 | 40.84 | 8.12 | 1.84 | 0.84 |
| 5374-A5403-36-353 | + | 6.66 | 29.27 | 13.98 | 40.82 | 6.26 | 1.77 | 0.83 |
| 5374-A5403-36-353 | + | 6.15 | 30.32 | 13.67 | 40.76 | 5.95 | 1.92 | 0.89 |
| average | | 6.37 | 30.23 | 12.35 | 40.95 | 7.03 | 1.86 | 0.86 |
| 5374-A5403-36-489 | + | 6.57 | 34.87 | 10.56 | 37.1 | 7.23 | 2.34 | 1.09 |
| 5374-A5403-36-489 | + | 6.25 | 37.1 | 8.43 | 37.65 | 7.05 | 2.33 | 1 |
| 5374-A5403-36-489 | + | 6.36 | 36.22 | 10.68 | 36.18 | 6.88 | 2.39 | 1.08 |
| 5374-A5403-36-489 | + | 6.29 | 36.28 | 8.69 | 38.06 | 7.08 | 2.33 | 1.04 |
| 5374-A5403-36-489 | + | 6.26 | 36.6 | 8.33 | 37.79 | 7.25 | 2.44 | 1.11 |
| average | | 6.35 | 36.21 | 9.34 | 37.36 | 7.10 | 2.37 | 1.06 |
| Control | | | | | | | | |
| 5374-A5403-36-341 | − | 10.7 | 6 | 24.46 | 50.9 | 6.29 | 0.53 | 0.61 |
| 5374-A5403-36-341 | − | 11.2 | 4.92 | 20.68 | 54.35 | 7.37 | 0.47 | 0.57 |
| 5374-A5403-36-341 | − | 11.27 | 4.27 | 23.71 | 52.72 | 6.55 | 0.43 | 0.53 |
| 5374-A5403-36-341 | − | 11.33 | 4.78 | 20.4 | 54.38 | 7.58 | 0.46 | 0.55 |
| 5374-A5403-36-341 | − | 11.55 | 4.52 | 18.59 | 55.07 | 8.69 | 0.46 | 0.56 |
| null segregant Ave | | 11.21 | 4.90 | 21.57 | 53.48 | 7.30 | 0.47 | 0.56 |

The results of the fatty acid compositional analysis for transformed 5378 soybean plants are shown in Table 3. Seeds of soybean plants transformed to express Garm FatA1 from the 7S promoter produced increased levels of stearate over those levels observed in seeds of nontransformed control plants. In the seed oil of some T1 5378 transgenic soybean, stearate levels of as high as approximately 53% of the fatty acids were obtained, while levels of approximately 4% were observed in nontransformed control plants.

TABLE 3

| STRAIN ID | GUS | % 16:0 | % 18:0 | % 18:1 | % 18:2 | % 18:3 | % 20:0 | % 22:0 |
|---|---|---|---|---|---|---|---|---|
| 5378-A5403-28 | + | 6.27 | 41.81 | 8.64 | 34.22 | 5.13 | 2.62 | 1 |
| 5378-A5403-28 | + | 6.3 | 42.63 | 10.15 | 32.76 | 4.16 | 2.55 | 0.87 |
| 5378-A5403-28 | + | 6.48 | 43.11 | 7.47 | 33.72 | 5.3 | 2.61 | 1.04 |
| 5378-A5403-28 | + | 6.48 | 43.12 | 9.32 | 32.97 | 4.14 | 2.64 | 1.02 |
| AVERAGE | | 6.38 | 42.67 | 8.90 | 33.42 | 4.68 | 2.61 | 0.98 |
| 5378-A5403-48 | + | 8.19 | 25.51 | 12.37 | 44.21 | 6.85 | 1.62 | 0.88 |
| 5378-A5403-48 | + | 7.74 | 33.77 | 12.13 | 36.33 | 6.41 | 2.23 | 1.05 |
| 5378-A5403-48 | + | 7.42 | 40.06 | 9.82 | 30.97 | 7.26 | 2.84 | 1.23 |
| 5378-A5403-48 | + | 7.89 | 45.26 | 5.73 | 30.23 | 6.8 | 2.71 | 1.06 |

TABLE 3-continued

| STRAIN ID | GUS | % 16:0 | % 18:0 | % 18:1 | % 18:2 | % 18:3 | % 20:0 | % 22:0 |
|---|---|---|---|---|---|---|---|---|
| 5378-A5403-48 | + | 7.04 | 47.2 | 5.69 | 29.58 | 6.13 | 2.86 | 1.2 |
| AVERAGE | | 7.66 | 38.36 | 9.15 | 34.26 | 6.69 | 2.45 | 1.08 |
| 5378-A5403-59 | + | 9.96 | 47.1 | 9.17 | 22.11 | 4.12 | 4.78 | 2.3 |
| 5378-A5403-59 | + | 7.06 | 47.3 | 4.44 | 29.02 | 7.17 | 3.31 | 1.44 |
| 5378-A5403-59 | + | 11.72 | 50.5 | 4.69 | 20.86 | 5.35 | 4.34 | 1.93 |
| 5378-A5403-59 | + | 7.55 | 51.95 | 4.99 | 24.53 | 5.02 | 4 | 1.72 |
| AVERAGE | | 9.07 | 49.21 | 5.82 | 24.13 | 5.42 | 4.11 | 1.85 |
| 5378-A5403-60 | + | 7.7 | 35.2 | 6.09 | 37.85 | 8.77 | 2.74 | 1.34 |
| 5378-A5403-60 | + | 7.19 | 35.53 | 5.86 | 38.36 | 8.57 | 2.79 | 1.41 |
| 5378-A5403-60 | + | 7.27 | 36.4 | 5.51 | 37.78 | 8.61 | 2.78 | 1.35 |
| 5378-A5403-60 | + | 9.01 | 52.21 | 1.71 | 23.14 | 7.62 | 4.41 | 1.59 |
| 5378-A5403-60 | + | 9.83 | 52.94 | 1.77 | 21.85 | 7.59 | 4.28 | 1.42 |
| AVERAGE | | 8.2 | 42.46 | 4.19 | 31.80 | 8.23 | 3.40 | 1.42 |
| 5378-A5403-69 | + | 11.67 | 4.67 | 18.46 | 55.85 | 7.93 | 0.43 | 0.47 |
| 5378-A5403-69 | + | 8.69 | 13.65 | 19.02 | 48.86 | 7.19 | 1.13 | 0.9 |
| 5378-A5403-69 | + | 8.13 | 18.5 | 14.7 | 48.52 | 7.4 | 1.41 | 0.83 |
| 5378-A5403-69 | + | 7.1 | 21.26 | 12.86 | 48.93 | 7.1 | 1.43 | 0.89 |
| 5378-A5403-69 | + | 8.04 | 44.02 | 8.09 | 28.04 | 7.34 | 2.96 | 1.16 |
| AVERAGE | | 8.73 | 20.42 | 14.63 | 46.04 | 7.39 | 1.47 | 0.85 |
| 5378-A5403-103 | + | 9.31 | 40.01 | 8.73 | 30.52 | 7.08 | 2.85 | 1.04 |
| 5378-A5403-113 | + | 7.41 | 49.06 | 4.91 | 28.83 | 5.45 | 2.91 | 1.06 |
| 5378-A5403-113 | + | 11.01 | 49.44 | 4.88 | 22.53 | 7.15 | 3.24 | 1.1 |
| 5378-A5403-113 | + | 7.03 | 49.79 | 4.09 | 29.08 | 5.9 | 2.79 | 1 |
| 5378-A5403-113 | + | 8.32 | 51.04 | 4.29 | 27.06 | 5.1 | 2.91 | 0.92 |
| 5378-A5403-113 | + | 8.52 | 52.59 | 3.69 | 26.35 | 4.64 | 2.93 | 0.86 |
| AVERAGE | | 8.46 | 50.38 | 4.37 | 26.77 | 5.65 | 2.96 | 0.99 |
| Control | | | | | | | | |
| A5403 | − | 11.62 | 4.3 | 24.26 | 49.84 | 7.47 | 0.48 | 0.57 |
| A5403 | − | 12.32 | 4.24 | 21.93 | 52.32 | 7.49 | 0.44 | 0.46 |
| A5403 | − | 12.64 | 4.25 | 20.49 | 53.42 | 7.81 | 0.43 | 0.51 |
| A5403 | − | 12.17 | 4.22 | 21.56 | 52.48 | 8.15 | 0.44 | 0.51 |
| A5403 | − | 11.68 | 4.32 | 25.68 | 49.67 | 7.06 | 0.48 | 0.54 |
| AVERAGE | | 12.09 | 4.27 | 22.78 | 51.55 | 7.60 | 0.45 | 0.52 |

In T3 seed of selected T2 soybean lines, increases in stearate of as high as approximately 53% of the total fatty acid composition were obtained (Table 4), similar to those levels obtained from seed oil from T1 5378 soybean lines. Furthermore, similar to the 5374 soybean plants, decreases in palmitate, oleate and linoleate were observed in both the T2 and T3 seed oil. In addition, increases in saturates greater than C18:0 are also obtained in both the T2 and T3 generations.

TABLE 4

| STRAIN ID | GUS | 16:0 | 18:0 | 18:1 | 18:2 | 18:3 | 20:0 | 22:0 |
|---|---|---|---|---|---|---|---|---|
| 5378-A5403-48-269 | + | 8.63 | 50.62 | 5.5 | 23.07 | 7.4 | 3.34 | 1.14 |
| 5378-A5403-48-269 | + | 8.27 | 53.31 | 4.54 | 23.14 | 6.2 | 3.26 | 1.09 |
| 5378-A5403-48-269 | + | 8.6 | 51.92 | 4.84 | 22.65 | 7.27 | 3.43 | 1.01 |
| 5378-A5403-48-269 | + | 8.62 | 51.62 | 4.39 | 23.2 | 7.43 | 3.46 | 1.06 |
| 5378-A5403-48-269 | + | 9.07 | 50.57 | 4.77 | 22.61 | 7.97 | 3.52 | 1.22 |
| average | | 8.64 | 51.61 | 4.81 | 22.93 | 7.25 | 3.40 | 1.10 |
| 5378-A5403-113-304 | + | 6.99 | 49.4 | 4.23 | 29.37 | 6.12 | 2.73 | 0.98 |
| 5378-A5403-113-304 | + | 6.79 | 50.25 | 3.77 | 28.53 | 6.76 | 2.74 | 0.99 |
| 5378-A5403-113-304 | + | 6.79 | 50.19 | 3.73 | 28.8 | 6.61 | 2.75 | 0.98 |

TABLE 4-continued

| STRAIN ID | GUS | 16:0 | 18:0 | 18:1 | 18:2 | 18:3 | 20:0 | 22:0 |
|---|---|---|---|---|---|---|---|---|
| 5378-A5403-113-304 | + | 6.34 | 47.67 | 4.08 | 30.03 | 7.96 | 2.77 | 1.01 |
| 5378-A5403-113-304 | + | 6.81 | 49.89 | 3.93 | 29.16 | 6.43 | 2.63 | 0.92 |
| average |  | 6.74 | 49.48 | 3.95 | 29.18 | 6.78 | 2.72 | 0.98 |
| 5374-A5403-36-341 | − | 10.7 | 6 | 24.46 | 50.9 | 6.29 | 0.53 | 0.61 |
| 5374-A5403-36-341 | − | 11.2 | 4.92 | 20.68 | 54.35 | 7.37 | 0.47 | 0.57 |
| 5374-A5403-36-341 | − | 11.27 | 4.27 | 23.71 | 52.72 | 6.55 | 0.43 | 0.53 |
| 5374-A5403-36-341 | − | 11.33 | 4.78 | 20.4 | 54.38 | 7.58 | 0.46 | 0.55 |
| 5374-A5403-36-341 | − | 11.55 | 4.52 | 18.59 | 55.07 | 8.69 | 0.46 | 0.56 |
| null segregant Ave |  | 11.21 | 4.90 | 21.57 | 53.48 | 7.30 | 0.47 | 0.56 |

The above results demonstrate that by expression of an acyl-ACP thioesterase with substantial activity towards 18:0 acyl-ACP substrates, and capable of producing C18:0 in seed tissue of soybean plants, it is now possible to increase the levels of stearate in the seed oil of soybean.

Example 4

Composition of High Stearate Soybean Oil

In this particular case, soybean variety Hartz H4152 (also known as HS-2) was developed with a unique fatty acid composition of about 24% or above stearate and below about 3%, preferably about 2.5% linolenate. H4152 was derived from the cross between a soybean line with high stearate content (H90-127-113, also known as HS-1) and a line with low linolenic content (N85-2176). H90-127-113 is a Hartz variety derived from a cross between Hartz variety H5668 and soybean line A6. A6 is a soybean mutant with high stearate seed content (28.1%) released in 1981 by Iowa State University (Hammond, E. G. and W. R. Fehr. 1983. Registration of A6 germplasm line of soybean. Crop Sci. 23: 192-193). The high stearate content in line A6 has been determined to be conditioned by a single recessive gene, fas-a (Graef, G. L., W. R. Fehr, and E. G. Hammond. 1985. Inheritance of three stearic acid mutants of soybean. Crop Sci. 25: 1076-1079). N85-2176 is a release from North Carolina State University selected for its low linolenate seed content.

The $F_1$ seeds from the cross between H90-127-113 and N85-2176 were grown in the greenhouse in November and December. In February, small portions of the $F_2$ seeds opposite the embryo were removed and analyzed in the laboratories of Hartz Seed Co. for fatty acid composition using a gas chromatography. $F_2$ seed number 27 was selected for its high stearate and low linolenate levels and was grown in the greenhouse. The $F_3$ seed from plant #27 were planted in the field at Stuttgart, Ariz. in the following summer. Ten agronomically desirable $F_3$ plants with desirable fatty acid composition were selected, and $F_4$ progeny rows from those plants were planted at Stuttgart in the summer. Twenty agronomically desirable, uniform single plants were selected from row number 4. The $F_5$ progeny of those 20 plants was planted in single rows in a winter nursery in Santa Isabel, Puerto Rico. Ten uniform, single rows were harvested and bulked. The resulting seed was grown in a 0.2 acre breeder increase at Stuttgart, Ariz. during the following summer, forming the foundation for Hartz variety H4152.

TABLE 5

| | Fatty acid distributions of soybean oil | | | | |
|---|---|---|---|---|---|
| Soybean oil | Palmitic C16:0 | Stearic C18:0 | Oleic C18:1 | Linoleic C18:2 | Linolenic C18:3 |
| Common | 11 | 4 | 23 | 53 | 8 |
| High stearate (H4152) | 10 | 21 | 22 | 41 | 3 |

The composition of the high stearate soybean oil is unique in that it has low linoleic and linolenic and high oleic and stearic fatty acids. This improves the stability of the oil to oxidative degradation and also changes the triglyceride composition, resulting in the formation of compounds that have a higher melting point than those found in common soybean oil. The melting point of high stearate soybean oil is below room temperature, but solid fats are present that crystallize when the oil is stored at room temperature.

Example 5

Stability of High Stearate Soybean Oil

TABLE 6

| | Stability assays of soybean oil | |
|---|---|---|
| Stability criteria | Common soybean oil | High stearate soybean oil |
| Inherent stability | 7.0 | 3.9 |
| Calculated iodine value | 132 | 101 |
| Active oxygen method | 8-10 | 40 |

Inherent stability is a calculated relative reactivity with oxygen, with higher values denoting a greater predisposition to oxidation (M. Erickson and N. Frey, *Food Technology,* 50: 63-68 (1994)). Iodine values represent calculated reactivities with elemental iodine, with higher values indicating greater reactivities (Official and Tentative Methods, American Oil Chemists' Society, Cd 1b-87, Champaign, Ill.). The active oxygen method assay simulates thermal breakdown encountered during cooking, with higher values representing greater thermal stability (Official and Tentative Methods, American Oil Chemists' Society, Cd 12-57(93), Chanpaign, Ill.). The increase in saturated and monounsaturated fatty acids, and the decrease in polyunsaturated fatty acids in high stearate soybean oil results in a greater thermal stability when compared to common soybean oil. The greater thermal stability of high stearate soybean oil when compared to common soybean oil agrees with predictions based upon the calculated inherent stabilities and iodine values.

Example 6

Solids Profile of Soybean Oils

TABLE 7

Solids present at various temperatures

| Oil type | Solids present at temperature | | | | |
|---|---|---|---|---|---|
| | 50° F. | 70° F. | 80° F. | 92° F. | 104° F. |
| Common soybean oil | — | — | — | — | — |
| High stearate (H4152) | 9.8 | — | — | — | — |
| Interesterified high stearate | 7.0 | 3.5 | 3.0 | 2.0 | 0.7 |

Solids were evaluated by the solids fat index using dilatometry. Values represent percent solids in a sample at the given temperature. Interesterified high stearate oil was prepared by interesterification according to the method of Erickson (Practical Handbook of Soybean Processing and Utilization, American Oil Chemists' Society Press, Champaign Ill., 1995). In contrast, soybean oil A6 having high stearic, normal levels of palmitic and linolenic, and low levels of oleic and linoleic acids, has no solids present at 24.7° C. and higher temperatures.

Example 7

Application of High Stearate Soybeans in Soy Based Foods

A. To prepare tofu and soymilk, 50 grams of high stearate soybeans were soaked in 150 grams water overnight and drained. Soybeans were rinsed with water. 185 grams of boiling water was added, and the mixture pureed. 315 grams of water were added, and the mixture heated to 100° C. for 10 minutes. Okara (filtered solids) was extracted using the Juiceman Junior machine (Salton Maxim, Mt. Prospect, Ill.) to dehull the beans. The hot soymilk should be approximately 8% solids. For firm tofu, 1.5 grams glucono-5-lactone (Aldrich, Milwaukee, Wis.) was added. The liquid was allowed to coagulate for 15 to 20 minutes at 90° C. with light stirring. The liquid was allowed to cool and form tofu.

B. To prepare soymilk, 150 grams of high stearate soybeans were soaked in 500 mL water overnight and drained. Soaked soybeans were rinsed with water. The beans were equally divided into two portions. Each portion was ground with 400 mL water in an Oster blender (Sunbeam, Delray Beach, Fla.) at the highest speed for 1.5 minutes. The combined slurry from the two portions was manually filtered through cloth. The solid residue was discarded. The filtrate was heated to 95° C. for 10 minutes to prepare soymilk. To prepare tofu, the hot soymilk was cooled to about 75° C., and 5 grams of either calcium sulfate or glucono-8-lactone was added. The mixture was allowed to stand for 30 minutes to form curd, which became silken tofu. To prepare firm tofu, the hot curd was broken, placed in a mold, and pressed to release the whey.

Tofu prepared from high stearate oil soybeans had a consistency that was firmer and more creamy than tofu prepared from standard control soybeans.

Example 8

Applications of Full Fat Soy Flour in Baked Foods

High stearate soybeans were processed into full fat soy flour using the standard industry protocol (Practical Handbook of Soybean Processing and Utilization, American Oil Chemists' Society Press, Champaign Ill., 1995). The flour can be added to baked products at high levels (15-20%) to increase the protein content without affecting the texture of the baked products. Flour obtained from high stearate soybeans can be used in an array of food products including candies, gravies, sauces, frozen desserts, pastas, meat products, and baked goods.

Example 9

Margarine Formulation Using High Stearate Soybean Oil

TABLE 8

Margarine composition

| Ingredient | Weight percent |
|---|---|
| Water | 16.85 |
| Whey protein | 0.4 |
| Salt | 1.9 |
| Lecithin | 0.4 |
| Monoglyceride (Super G7, AC Humko Co) | 0.45 |
| Sodium benzoate | 0.001 |
| Interesterified high stearate oil | 80.0 |
| Flavor, color to 100% (I-1435, Fries & Fries) | |

The oil was heated to 65° C. in a microwave oven. Flavors were withheld and added to the oil phase immediately before the oil phase was combined with the remaining components which had been heated to 50° C. in a microwave oven. The two phases were combined and mixed for 20 minutes at 2000 rpm in a Dispermat unit (VMA-Getzmann, Germany) maintained at 60° C. The margarine was filled into one pound tubs and placed at 40° C. for crystallization. The margarine product was easily spreadable when removed from refrigeration after one day, and after long term storage of four weeks. The margarine exhibited good room temperature stability as well as excellent flavor release and structure.

Example 10

Formulation of all-Purpose Shortenings with Interesterified High Stearate Oil Commercial shortenings, such as CRISCO (Proctor and Gamble, Cincinnati, Ohio), are composed of a hydrogenated soybean oil combined with a fully hydrogenated cottonseed oil component and an emulsifier such as a monoglyceride. The soybean oil basestocks generally have a trans fatty acid content of greater than 15% (w/w), and frequently greater than 25% (w/w). The interesterified high stearate soybean oil has sufficient solids such that when combined with the fully hydrogenated cottonseed oil and monoglyceride, it gives a texture and consistency similar to the CRISCO product upon votation (rapid chilling and working of fat, Weiss, T. J., Food oils and Their Uses, Avi Publishing Co., Westport, Conn., 1983) and crystallization. Nitrogen is added to the formulation to modify the final density and solidity of the product. A 15% overrun of gas corresponds to a 15% reduction in density of the shortening in comparison to the density before addition of nitrogen.

TABLE 9

Shortening formulation

| Component | Percent by mass |
| --- | --- |
| Interesterified high stearate oil | 89.2 |
| Cottonseed oil (5 iodine value max.) | 7.8 |
| Monoglyceride (Super G7, AC Humko Co) | 3.0 |
| Nitrogen gas | 15% overrun |

Example 11

Shelf Life Testing

Non-hydrogenated oils are preferred over partially hydrogenated oils due to costs and improved acceptance by the consumer. However, the short shelf stability of non-hydrogenated oils severely limit their food applications. The interesterified high stearate soybean oil was used in a potato chip rancidity assay to determine the applicability in the preparation of fried foods.

TABLE 10

Schaal oven test

| Oil | Days to detect rancid odor |
| --- | --- |
| Common soybean oil | 2-3 |
| All-purpose shortening (CRISCO) | 6-7 |
| Interesterified high stearate oil (all-purpose shortening formulation) | 11 |

The rancidity assay was performed using a Schaal oven test at 62° C. (Warner, K. and Eskin, N. M., Methods to Assess Quality and Stability of Oils and Fat-Containing Foods, American Oil Chemists' Society Press, Chanpaign, Ill., 1995). Interesterified high stearate oil demonstrated a marked increase in stability, as indicated by the longer duration of time required to detect an undesirable odor.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A soybean seed comprising an introduced nucleic acid sequence having in the 5' to 3' direction of transcription: a promoter that is functional in a soybean seed cell and a DNA sequence encoding a plant FatA thioesterase, wherein said plant FatA thioesterase has the sequence of *Garcinia mangostana* (Garm) FatA1 (SEQ ID NO: 2), and said plant FatA thioesterase has a high relative activity for 18:0-acyl-acyl-carrier protein (ACP) as compared to 16:0-ACP, and the fatty acid moieties in the soybean oil from said soybean seed comprise greater than about 20% stearate and less than about 53% stearate.

2. The soybean seed of claim 1, wherein said DNA sequence encoding a plant FatA thioesterase is SEQ ID NO:1.

3. The soybean seed of claim 1, wherein said introduced nucleic acid sequence has a transcription termination sequence in the 3' direction of said DNA sequence encoding a plant FatA thioesterase.

4. The soybean seed of claim 1, wherein said soybean oil contains about 50 weight percent or greater stearate expressed as a component of total fatty acids contained in the soybean seed oil.

5. The soybean seed of claim 1, wherein said oil comprises 25 percent or greater of said total fatty acids in a saturated-unsaturated-saturated form.

6. The soybean seed of claim 1, wherein said plant FatA thioesterase 16:0 activity represents only approximately 3% of said plant FatA thioesterase 18:1 activity.

7. The soybean seed of claim 1, wherein said fatty acid moieties including 16:0, 18:0, 20:0, and 22:0 comprise at least 30 percent of the total fatty acids as a percentage of weight.

8. The soybean seed of claim 1, wherein said fatty acid moieties including 16:0, 18:0, 20:0, and 22:0 comprise at least 50 percent of the total fatty acids as a percentage of weight.

9. The soybean seed of claim 1, wherein the percentage of saturated fatty acid moieties greater than 18:0 are increased as compared to null progeny which do not contain the Garm FatA1 transgene.

10. The soybean seed of claim 1, wherein stearate levels increase 4 fold to approximately 7 fold as compared to seeds from nontransformed control plants.

11. The soybean seed of claim 1, wherein said promoter functional in a soybean plant seed cell is selected from the group consisting of an ACP transcriptional initiation control region, a napin transcriptional initiation control region, a β-conglycinin 7S transcriptional initiation control region, *Lesquerella* hydroxylase promoter, and a stearoyl-ACP desaturase promoter.

12. The soybean seed of claim 11, wherein said promoter that is functional in a soybean seed cell is said β-conglycinin 7S transcriptional initiation control region.

13. The soybean seed of claim 11, wherein said promoter that is functional in a soybean seed cell is said napin transcriptional initiation control region.

14. The soybean seed of claim 1, wherein said promoter that is functional in a soybean seed cell is preferentially expressed in said soybean cell.

15. The soybean seed of claim 1, wherein said encoding sequence has no activity on 16:0 substrates.

16. The soybean seed of claim 1, wherein said promoter is from a gene preferentially expressed in plant seed tissue.

17. The soybean seed of claim 1, wherein said DNA sequence encoding a plant FatA thioesterase is from the genus *Garcinia*.

18. The soybean seed of claim 1, wherein said fatty acid moieties in the soybean oil from said soybean seed comprise about 40% by weight stearate.

19. The soybean seed according to claim 1 comprising about 50 percent or greater stearate as the fatty acid found at the sn-1 and sn-3 positions of seed triglycerides.

20. The soybean seed according to claim 18 comprising about 60 percent or greater stearate as the fatty acid found in said sn-1 and sn-3 positions of seed triglycerides.

21. The soybean seed according to claim 4 comprising about 75 percent or greater stearate as the fatty acid found in said sn-1 and sn-3 positions of seed triglycerides.

22. The soybean seed according to claim 19, and comprising oleic acid as the predominant fatty acid at the sn-2 position of seed triglycerides.

* * * * *